(12) United States Patent
Lin et al.

(10) Patent No.: US 7,485,716 B2
(45) Date of Patent: Feb. 3, 2009

(54) STEREOSELECTIVE SYNTHESIS OF β-NUCLEOSIDES

(75) Inventors: Ko-Chung Lin, Lexington, MA (US); Wensen Li, Holmdel, NJ (US)

(73) Assignee: Pharmaessentia Corp., Taipei (TW)

( * ) Notice: Subject to any disclaimer, the term of this patent is extended or adjusted under 35 U.S.C. 154(b) by 146 days.

(21) Appl. No.: 11/416,636

(22) Filed: May 2, 2006

(65) Prior Publication Data
US 2007/0015914 A1  Jan. 18, 2007

Related U.S. Application Data

(60) Provisional application No. 60/676,787, filed on May 2, 2005.

(51) Int. Cl.
*C07H 21/00* (2006.01)
(52) U.S. Cl. .................................................... 536/25.3
(58) Field of Classification Search .................. None
See application file for complete search history.

(56) References Cited

U.S. PATENT DOCUMENTS

| | | | |
|---|---|---|---|
| 4,526,988 A | 7/1985 | Hertel | |
| 4,692,434 A | 9/1987 | Hertel | |
| 4,751,221 A | 6/1988 | Watanabe et al. | |
| 4,760,137 A | 7/1988 | Robins et al. | |
| 4,808,614 A | 2/1989 | Hertel | |
| 4,954,623 A | 9/1990 | Nagarajan | |
| 4,965,374 A | 10/1990 | Chou et al. | |
| 5,006,646 A * | 4/1991 | Itoh et al. | 536/28.54 |
| 5,216,145 A | 6/1993 | Raifeld | |
| 5,223,608 A | 6/1993 | Chou et al. | |
| 5,401,838 A | 3/1995 | Chou | |
| 5,424,416 A | 6/1995 | Jones | |
| 5,434,254 A | 7/1995 | Chou et al. | |
| 5,521,294 A | 5/1996 | Wildfeuer | |
| 5,594,124 A | 1/1997 | Chou | |
| 5,648,473 A | 7/1997 | Chou | |
| 5,808,048 A | 9/1998 | Berglund | |
| 5,821,357 A | 10/1998 | Chou et al. | |
| 5,945,547 A | 8/1999 | Chou et al. | |

FOREIGN PATENT DOCUMENTS

EP  0 184 365  8/1993

OTHER PUBLICATIONS

Yasumoto et al. J. Med. Chem. (1977), vol. 20, pp. 1592-1594.*
Hertel et al., "Synthesis of 2-Deoxy-2,2-difluoro-D-ribose and 2-Deoxy-2,2-difluoro-D-ribofuranosyl Nucleosides", J. Org. Chem., 53:2406-2409, 1988.

* cited by examiner

*Primary Examiner*—Patrick T Lewis
(74) *Attorney, Agent, or Firm*—Occhiuti Rohlicek & Tsao LLP

(57) ABSTRACT

This invention relates to a process for stereoselectively preparing a nucleoside of the following formula:

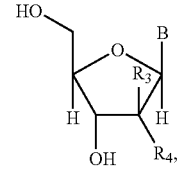

wherein $R_3$, $R_4$, and B are defined herein. The process includes reacting a furanose compound with a nucleobase in the presence of a halide salt. Also disclosed is another process for stereoselectively synthesizing an intermediate that can be used to make the starting compound in the first-mentioned process.

20 Claims, No Drawings

STEREOSELECTIVE SYNTHESIS OF β-NUCLEOSIDES

RELATED APPLICATIONS

This application claims priority to U.S. provisional application No. 60/676,787, filed May 2, 2005, the contents of which are incorporated herein by reference.

BACKGROUND

2'-Deoxynucleosides and their analogues are therapeutically important agents. For example, 2'-deoxy-2,2'-difluorocytidine hydrochloride can be used to treat viral infection and cancer (see, e.g., U.S. Pat. Nos. 4,526,988 and 4,808,614).

In general, 2'-deoxynucleosides each have more than one chiral center and can occur as multiple stereoisomers. Not all stereoisomers are therapeutically active. Several stereoselective synthetic routes for 2-deoxy-β-nucleosides have been developed. However, none of them are satisfactory. For example, U.S. Pat. No. 5,648,473 describes a synthetic method that produces β anomer-enriched 2-deoxy-β-nucleoside from α-anomer of furanose. This method is economically ineffective, as it requires an anomerically pure or enriched starting material.

There is a need to develop a more effective route for stereoselectively synthesizing 2'-deoxynucleosides.

SUMMARY

One aspect of this invention relates to a process including reacting a furan compound of the following formula:

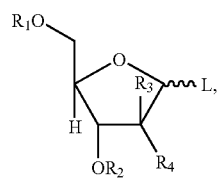

in which each of $R_1$ and $R_2$ independently is a hydroxy protecting group, or $R_1$ and $R_2$, together, are $C_{1-3}$ alkylene; each of $R_3$ and $R_4$ independently is H, halo, alkoxy, alkyl, or aryl, and L is a leaving group;

with a compound of the following formula:

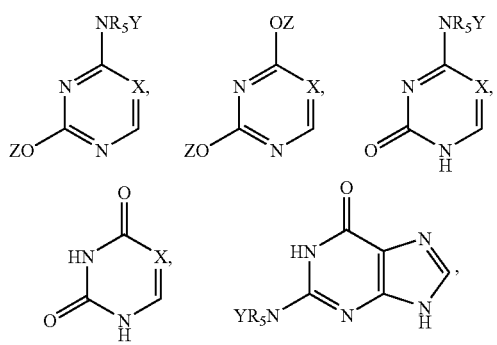

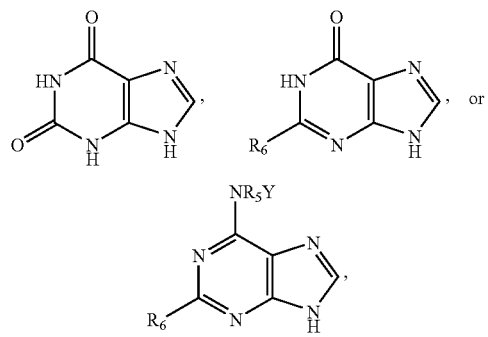

in which $R_5$ is H, alkyl, or aryl; $R_6$ is H, alkyl, alkenyl, halo, or aryl; X is N or C—R', R' being H, alkyl, alkenyl, halo, or aryl; Y is an amino protecting group, and Z is a hydroxy protecting group;

in the presence of a halide salt at 50-200° C. to stereoselectively form a β-nucleoside of the following formula:

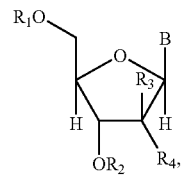

in which $R_1$, $R_2$, $R_3$, and $R_4$ are defined above and B is

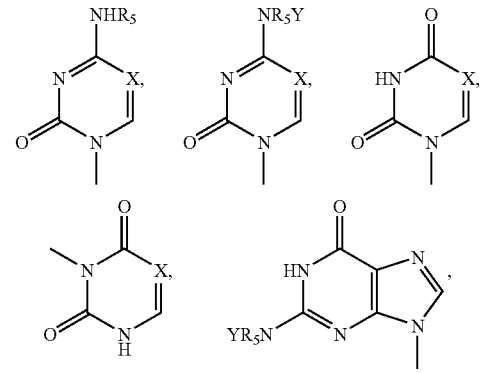

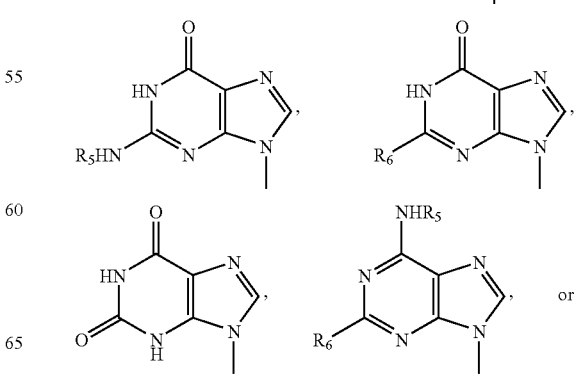

-continued

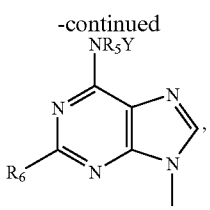

in which X, Y, $R_5$, and $R_6$ are defined above. The reaction can be carried out with microwave or in a solvent such as toluene or chlorobenzene.

The resulting β-nucleoside can be deprotected to form 3,5-dihydroxy β-nucleoside of the following formula:

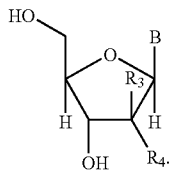

An example of the just-described synthetic process is reacting a furanose compound with

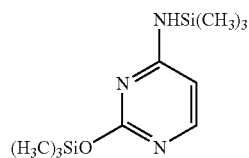

to form, after deprotection, a β-nucleoside of the following formula:

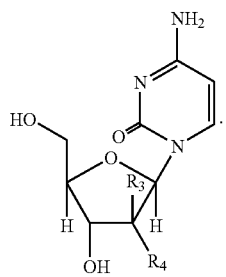

The method of this invention may further include one or more of the following steps, through which the above-described furan compound are prepared:

(1) reacting an aldehyde of the following formula:

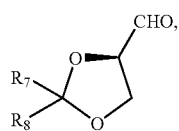

wherein each of $R_7$ and $R_8$ independently is H, halo, or alkyl; with an ester of the following formula:

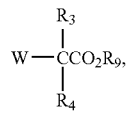

wherein $R_3$ and $R_4$ are defined above and $R_9$ is alkyl or aryl; to form an alcohol of the following formula:

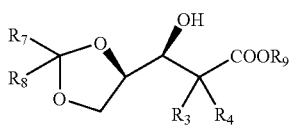

wherein $R_3$, $R_4$, $R_7$, $R_8$, and $R_9$ are defined above;

(2) converting the alcohol to a protected lactone of the following formula:

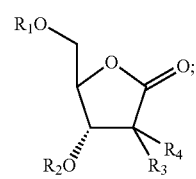

wherein $R_1$, $R_2$, $R_3$, and $R_4$ are defined above;

(3) reducing the protected lactone to a furanose of the following formula:

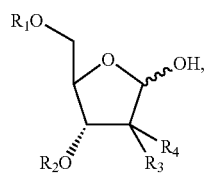

wherein $R_1$, $R_2$, $R_3$, and $R_4$ are defined above; and (4) transforming the furanose to the furan compound described above.

The term "alkyl" refers to a straight or branched hydrocarbon, containing 1-6 carbon atoms. Examples of alkyl groups include, but are not limited to, methyl, ethyl, n-propyl, i-propyl, n-butyl, i-butyl, and t-butyl. The term "alkoxy" refers to an O-alkyl radical. Examples of alkoxy groups include, but are not limited to, methoxy, ethoxyl, and butoxy. The term "alkylene" refers to a alkyl diradical group. Examples of "alkylene" include, but are not limited to, methylene and ethylene.

The term "alkenyl" refers to a straight or branched hydrocarbon having one or more carbon-carbon double bonds. Examples of alkenyl groups include, but are not limited to, ethenyl, 1-butenyl, and 2-butenyl.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl.

The term "alkoxycarbonyl" refers to an alkyl-O-carbonyl radical. Examples of alkoxycarbonyl groups include, but are not limited to, methoxycarbonyl, ethoxycarbonyl, and t-butoxylcarbonyl. The term "aroxycarbonyl" refers to an aryl-O-carbonyl radical. Examples of aroxycarbonyl groups include, but are not limited to, phenoxycarbonyl and 1-naphthalenoxycarbonyl. The term "aminocarbonyl" refers to a (R)(R') N-carbonyl radical in which each of R and R' independently is H, alkyl, or aryl. Examples of aminocarbonyl groups include, but are not limited to, dimethylaminocarbonyl, methylethylaminocarbonyl, and phenylaminocarbonyl.

Alkyl, aryl, alkenyl, and alkoxy mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, and heterocyclyl, in which the alkyl, alkenyl, alkynyl, alkyloxy, aryl, heteroaryl, cyclyl, and heterocyclyl may be further substituted.

The term "furanose" refers to a five-membered cyclic acetal form of a sugar.

Other features, objects, and advantages of the invention will be apparent from the description and the claims.

DETAILED DESCRIPTION

Referring to the actual example below, it was unexpectedly discovered that when a 1:1 anomeric mixture of furanose compound 1 is reacted with cytosine in the presence of sodium iodide at an elevated temperature, β-nucleoside 2 is formed preferentially over α-nucleoside with a ratio of β:α greater than 2:1. The reaction is shown in the following scheme:

includes reacting the furanose compound with a nucleobase in the presence of a halide salt.

Stereoselective synthesis is preparation of one stereoisomer preferentially over the other stereoisomers. As an example, the just-mentioned synthetic process affords one anomer of a nucleoside preferentially over the other.

The furanose compound used in this synthetic process contains a leaving group at its 1-position. The leaving group is a functional group that can depart, upon direct displacement or ionization, with the pair of electrons from one of its covalent bonds (see, e.g., F. A. Carey and R. J. Sundberg, *Advanced Organic Chemistry*, 3$^{rd}$ Ed. Plenum Press, 1990). Examples of leaving groups include, but are not limited to, methanesulfonate, triflate, p-toluenesulfonate, iodide, bromide, chloride, and trifluoroacetate. The furanose compound also contains two or more hydroxy protecting groups, which prevent the protected hrodroxy groups from interference. Examples of hydroxy protecting groups include, but are not limited to, alkyl, benzyl, allyl, acyl (e.g., benzoyl, acetyl, or HOOC—X—CO—, X being alkylene, alkenylene, cycloalkylene, or arylene), silyl (e.g., trimethylsilyl, triethylsilyl, and t-butyldimethylsilyl), alkoxylcarbonyl, aminocarbonyl (e.g., dimethylaminocarbonyl, methylethylaminocarbonyl, and phenylaminocarbonyl), alkoxymethyl, benzyloxymethyl, and alkylmercaptomethyl. The nucleobase used in this process may contain an amino protecting group to prevent the protected amino group from interference. Examples of amino protecting groups include, but are not limited to, alkyl, acyl, and silyl. Hydroxy and amino protecting groups have been discussed in T. W. Greene and P. G. M. Wuts, *Protective Groups in Organic Synthesis*, 2d. Ed., John Wiley and Sons (1991). Both protecting groups can be removed by conventional methods after the reaction. For example, the two protecting groups of 3,5-dihydroxy of compound 2 can be removed in any order to form 3,5-dihydroxy β-nucleoside 3 as shown in the following scheme:

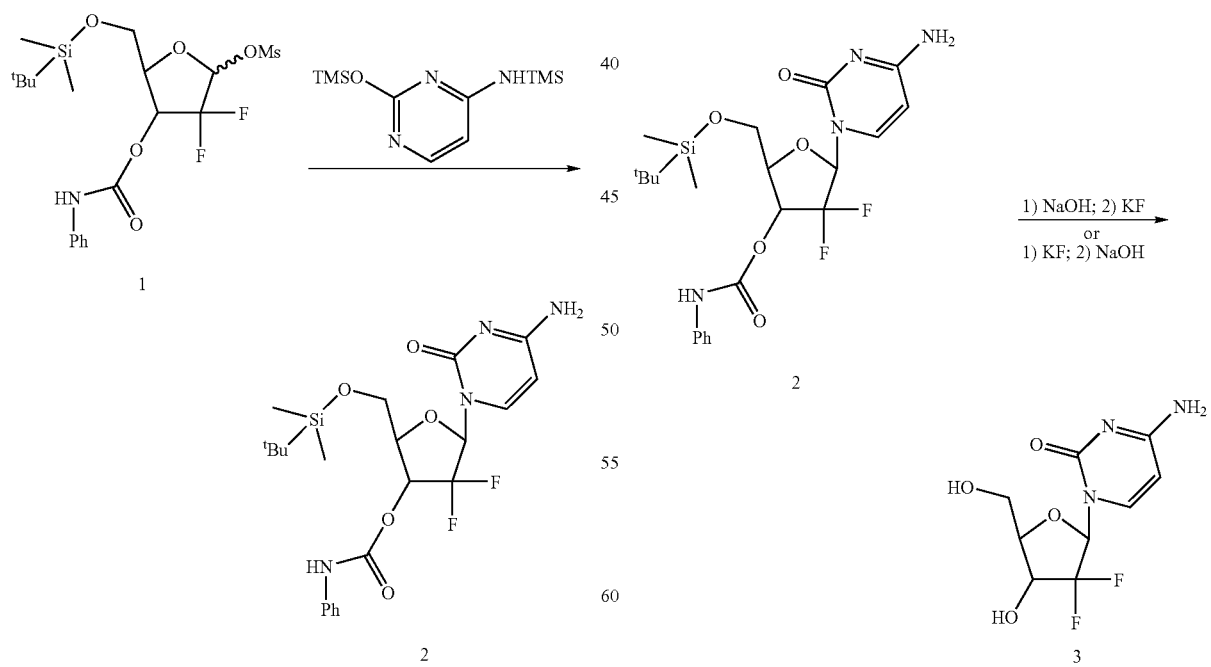

Thus, this invention features a synthetic process for stereoselectively preparing a β-nucleoside from an anomeric mixture of corresponding furanose. The synthetic process The above-mentioned synthetic process requires a halide salt, which is a salt containing at least one halide ion. Examples of halide salts include, but are not limited to, potassium iodide, lithium iodide, sodium iodide, magnesium iodide, zinc iodide, lithium bromide, sodium bromide, potassium bromide, magnesium bromide, and zinc bromide.

To practice this process, one can mix the required reactants and a halide salt in a solvent. Examples of suitable solvents include, but are not limited to, toluene, xylene, benzene, dichloromethane, chloroform, 1,2-dichloroethane, chlorobenzene, hexane, heptane, cyclohexane, hexane, heptane, cyclohexane, ethyl acetate, isopropyl acetate, n-butyl acetate, acetonitrile, acetone, methylethylketone, methylisopropylketone, or a mixture thereof. The halide salt can be employed in an equimolar amount, relative to one of the reactants. It can also be employed in a catalytical amount (e.g., 0.01 molar equivalents) or in an excess amount (e.g., 1.1-10 molar equivalents). The halide salt, the reactants, and the solvent can be added in an alternate sequence.

The reaction is preferably conducted at an elevated temperature, e.g., 50 to 200° C. Further, to facilitate this reaction, microwave, UV, or ultrasound can be used. As an example, the reaction vessel can be placed in an ultrasound bath during the reaction. As recognized by those skilled in the art, the reaction time varies depending on the types and the amounts of the reactants and halide salt, the reaction temperature, and the like.

The reactants required in this process are commercially available or can be made by methods well known in the art. For example, referring to the reaction shown below, U.S. Pat. No. 4,965,374 teaches a synthetic method of preparing 2-deoxy-2,2'-difluoro-1-oxoribose 5 and its enantiomer from a mixture of 2,2-difluoro-3(R)-hydroxy-3-(2,2-dimethyldioxolan-4-yl)propionate 4 and its 3(S) enantiomer. Also described in the '374 patent is an isolating method to obtain enantiomerically pure lactone 5.

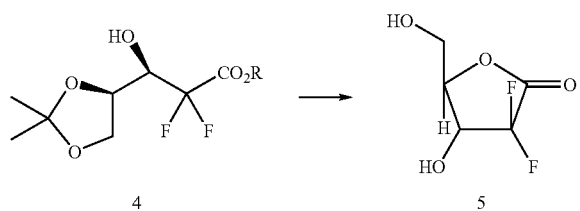

Latone 5 can be converted to furanose compound 1, a reactant in the just-described synthetic process, by protecting hydroxyl groups, reducing the carbonyl group to a hydroxy group, and subsequently reacting the hydroxy group with methanesulfonyl chloride. Other furanose compounds can also be made according to the same method with minor modification.

In the just-described synthetic method, propionate 4 is converted to lactone 5, and the enantiomer of propionate 4 is converted to the enantiomer of lactone 5. Lactone 5, which is enantiomerically pure, is an important starting material for synthesis of the furanose compound used in the above-described synthetic process. For preparation of β-nulceosides by this synthetic process, it is essential to obtain enantiomerically pure propionate 4 and its analogues. Referring to the actual example, it was unexpectedly discovered that reacting (R) 4-formyl-2,2-dimethyldioxolane 6 with an α-bromoacetate 7 in the presence of Zn and a Zn activating agent (e.g., $I_2$) gives propionate 4 with high enantiomeric purity, i.e., enantiomeric excess about 98%. The reaction is shown in the following scheme:

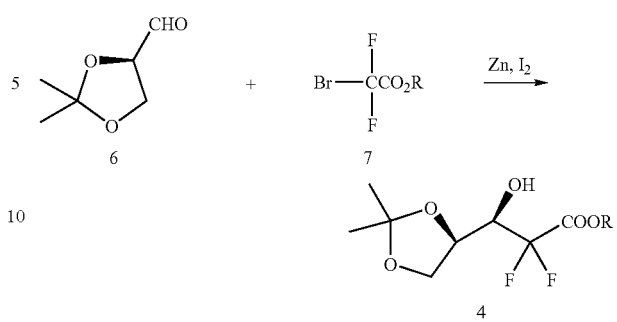

Thus, this invention also features a synthetic process for stereoselectively preparing (R) 3-hydroxypropionate 4 and its analogues. The synthetic process includes reacting (R) 4-formyl-2,2-dialkylldioxolane with an alkyl α-Br or α-I substituted acetate in the presence of Zn and a Zn activating agent. The Zn activating agent is a substance that activates Zn metal by reducing any oxidized Zn to atomic Zn. Examples of Zn activating agents include, but are not limited to, $I_2$, 1,2-dibromoethane, or 1,2-diiodoethane.

To practice this synthetic process, one can mix the required reactants and a Zn activating agent in a solvent. Examples of suitable solvents include, but are not limited to, dichloromethane, tetrahydrofuran (THF), benzene, chloroform, toluene, xylene, chlorobenzene, hexane, heptane, cyclohexane, hexane, heptane, cyclohexane with ethyl acetate, isopropyl acetate, n-butyl acetate, acetonitrile, 1,2-dichloroethane, and a combination thereof. The Zn activating agent may be employed in a catalytical amount, an equimolar amount, or an excess amount, relative to one of the reactants. The reaction can be carried out at −10 to 30° C. To facilitate the reaction, microwave, UV, or ultrasound can be used.

For either synthetic process described above, completion of the reaction can be monitored by any conventional method, e.g., ultra-violent spectrum, infrared spectrum, nuclear magnetic resonance, thin layer chromatography, gas chromatography, and high performance liquid chromatography. After the reaction is complete, the product can be separated from the reaction mixture by one or more conventional separation methods, such as chromatography, recrystalation, extraction, and distillation. It may be further purified to give higher enantiomeric purity by methods well known in the art. See, e.g., U.S. Pat. No. 5,223,608.

Without further elaboration, it is believed that the above description has adequately enabled the present invention. The following actual example is, therefore, to be construed as merely illustrative, and not limitative of the remainder of the disclosure in any way whatsoever. All of the publications cited herein, including patents, are hereby incorporated by reference in their entirety.

EXAMPLE

β-2-Desoxy-2,2'-difluorocytidine was synthesized according to the procedures described below:

Preparation of a 2,2-difluoro-3(R)-hydroxy-3-(2,2-dimethyldioxolan-4-yl)propionate Zn (3.6 g, 57.5 mmol) and $I_2$ (144 mg, 0.6 mmol) was added to a solution of (R)4-formyl-2,2-dimethyldioxolane (3 g, 23 mmol) and ethyl bromodifluoroacetate (4.7 g, 23 mmol) in THF (50 mL) at 25° C. The reaction vessel was agitated in an ultrasonic bath at 5-10° C. for 12 h. A solution of ethyl bromodifluoroacetate (4.7 g, 23 mmol) in THF (5 mL) was added and the resulting solution was irradiated for additional 12 h at 10° C. The reaction was quenched by a saturated aqueous NH$_4$Cl solution. The solution was filtered and concentrated in vacuo to ca. 5 mL, diluted with EtOAc (150 mL), washed with brine (15 mL), dried over Na$_2$SO$_4$, and concentrated in vacuo to give a crude product. The crude product was purified by flash column chromatography with 10-20% EtOAc-hexane to give a single compound of 2,2-difluoro-3 (R)-hydroxy-3-(2,2-dimethyldioxolan-4-yl)propionate (4.4 g, 75% yield) as a yellow liquid.

R$_f$=0.25 in 25% EtOAc-hexane;

$^1$H NMR (500 MHz, CDCl$_3$): δ 4.05-4.335 (m, 4 H), 4.01-4.04 (m, 2 H), 3.29 (br, 1 H), 1.32 (t, 3H, J=8 Hz), 1.30 (s, 3 H), 1.29 (s, 3 H);

$^{13}$C NMR (125 MHz, CDCl$_3$): δ 163.122 (t, C, J$_{C-F}$=30.5 Hz), 113.99 (dd, C, J$_{C-F}$=252 Hz, 254 Hz), 109.70 (C), 73.37 (CH), 71.56(t, CH, J$_{C-F}$=23 Hz), 65.60 (CH$_2$), 63.06 (CH$_2$), 26.09 (CH$_3$), 24.94 (CH$_3$), 13.74 (CH$_3$).

Preparation of 2-desoxy-2,2'-difluoro-1-oxoribose

To a solution of 2,2-difluoro-3(R)-hydroxy-3-(2,2-dimethyldioxolan-4-yl)propionate (6.0 g, 23.4 mmol) in MeOH—H$_2$O (2:1, 50 mL) was added Dowex 50WX8-100 (30.0 g) at 25° C. The solution was stirred for 48 h at ambient temperature and filtered through celite. The filtrate was concentrated in vacuo. The residue was purified by flash column chromatography with 70-100% EtOAc-hexane to give the desire compound (3.7 g, 95% yield) as a yellow oil.

R$_f$=0.5 in 75% EtOAc-hexane;

$^1$H NMR (400 MHz, DMSO): δ 5.79 (br, 1H), 4.48-4.64 (m, 1 H), 4.45-4.62 (m, 1 H), 3.97-4.02 (m, 1 H), 3.81-3.85 (m, 1 H);

$^{13}$C NMR (100 MHz, CDCl$_3$): δ191.96 (dd, C, J$_{C-F}$=35 Hz, 41 Hz), 131.07 (dd, C, J$_{C-F}$=301 Hz, 309 Hz), 94.01 (d, C, J$_{C-F}$=47 Hz), 76.37 (dd, CH, J$_{C-F}$=21 Hz, 31 Hz), 65.71 (CH$_2$).

Preparation of 5-t-butyldimethylsilyloxy-2-desoxy-2, 2'-difluoro-1-oxoribose

To DMF (40 mL) were sequentially added 2-desoxy-2,2'-difluoro-1-oxoribose (2.04 g, 12.1 mmoles), imidazole (1.23 g, 18 mmoles), and tert-butyldimethylsiliyl chloride (2.2 g, 14.52 mmoles) at room temperature under N$_2$. The reaction mixture was heated at 45° C. for 2 days, and then was cooled to room temperature. The resulting precipitate was filtered and was washed with EtOAc (100 mL×2). The combined organic solvent was then washed with a saturated aqueous NH$_4$Cl solution (50 mL), dried over MgSO4, filtered, and concentrated in vacuo to give a crude residue. The residue was purified by column chromatography eluted with a 96:4 n-hexane/EtOAc mixture to give 1.2 g of the title compound as a colorless oil.

$^1$H NMR (400 MHz, CDCl$_3$): δ 4.53-4.55 (m, 1 H), 4.25-4.27 (m, 1 H), 3.93-3.99 (m, 1 H), 3.78-3.82 (m, 1 H), 0.86-0.92 (m, 9 H), 0.04-0.14 (m, 6 H).

Preparation of 3-anilinycarbonyloxy-5-t-butyldimethylsilyloxy-2-desoxy-2,2'-difluoro-1-oxoribose 5-t-Butyldimethylsilyloxy-2-desoxy-2,2'-difluoro-1-oxoribose (1.6 g, 5.7 mmoles) and phenyl isocyanate (1.5 ml, 14.3 mmoles) were dissolved in anhydrous dichloromethane (20 ml). To this solution was added a solution of triethylamine (2.0 mL, 14.3 mmoles) in dichloromethane (10 mL) over a period of 10 minutes at 0° C under N$_2$. After the addition, the solution was warmed to room temperature and was stirred for an additional hour. It was then poured into saturated aqueous citric acid (50 mL) and extracted with dichloromethane (100 mL×3). The organic layers were combined, washed with brine, dried over MgSO$_4$, and concentrated in vacuo to give a crude residue. The residue was purified by column chromatography eluting with a mixture of 9:1 n-hexane/EtOAc to give 2.3 g (100%) of the title compound as a white solid.

$^1$H NMR (400 MHz, CDCl$_3$): δ 7.0-7.4 (m, 5H), 5.00-5.12 (m, 1H), 3.62-4.41 (m, 4 H), 0.87-0.93 (m, 9 H), 0.04-0.12 (m, 6 H);

$^{13}$C NMR (100 MHz, CDCl$_3$): δ 126 (CH), 121.52 (C), 112 (CH), 106 (CH), 96.17 (CH), 83.17 (CH), 69.58 (CH), 61.87 (CH$_2$), 25.50 (CH$_3$), 18.13 (C), −5.37 (CH$_3$).

Preparation of 3-anilinycarbonyloxy-5-t-butyldimethylsilyloxy-2-desoxy-2,2'-difluororibose A solution of 3-anilinycarbonyloxy-5-t-butyldimethylsilyloxy-2-desoxy-2,2'-difluoro-1-oxoribose (1.12 g, 2.8 mmoles) in anhydrous THF (70 mL) was added dropwise to a solution of LiAl(OtBu)$_3$H (4.3 g, 16.8 mmoles) in anhydrous THF (20 mL) at 0° C. The reaction mixture was stirred at 0° C. for 8 hours and at room temperature for additional 8 hours. The reaction was then quenched with MeOH (10 mL). The resulting mixture was poured into a 0.5 N HCl (30 mL) solution and extracted with dichloromethane (70 mL×3). The organic layers were combined, washed with a saturated aqueous NaHCO$_3$ solution, dried over MgSO$_4$, and concentrated in vacuo to give the crude title compound (1.0 g, 88% yield).

$^1$H NMR (400 MHz, CDCl$_3$): δ 7.0-7.4 (m, 5H), 5.00-5.12 (m, 1H), 3.62-4.41 (m, 4 H), 0.87-0.93 (m, 18 H), 0.04-0.12 (m, 12 H);

$^{13}$C NMR (100 MHz, CDCl$_3$): δ 126 (CH), 112 (CH), 106 (CH), 121.52 (C), 96.17 (CH), 83.17 (CH), 69.58 (CH), 61.87 (CH$_2$), 25.50 (CH$_3$), 18.13 (C), −5.37 (CH$_3$).

Preparation of 3-anilinycarbonyloxy-5-t-butyldimethylsilyloxy- 1 -methanesulfonyloxy-2-desoxy-2,2'-difluororibose Mesyl chloride (0.05 mL, 0.7 mmoles) in dichloromethane (2 mL) was added to a solution of 3-anilinycarbony-5-t-butyldimethylsilyloxy-2-desoxy-2,2-difluororibose (0.18 g, 0.45 mmoles) and triethyamine (0.13 mL, 0.9 mmoles) in dichloromethane (5 mL) at 0° C. The reaction solution was stirred at room temperature for 1.5 hours and was then concentrated in vacuo. The resulting residue was dissolved in dichloromethane (20 mL), washed with a saturated aqueous NaHCO$_3$ solution, saturated aqueous citric acid, brine, dried over MgSO$_4$, and concentrated in vacuo to give a crude product. The crude product was purified by column chromatography to afford 3-anilinycarbony-5-t-butyldimethylsilyloxy-1-methanesulfonyloxy-2-desoxy-2,2-difluororibose (65 mg, 31% yield). The product was further purified by crystallization from 2:1 methylene chloride/hexane.

$^1$H NMR (500 MHz, CDCl$_3$): δ 7.0-7.4 (m, 5H), 5.84 (apparent dd, 1H), 3.67-4.46 (m, 4 H), 0.83-0.92 (m, 18 H), 0.04-0.12 (m, 12 H);

$^{13}$C NMR (125 MHz, CDCl$_3$): δ 126 (CH), 121.12 (C), 112 (CH), 106 (CH), 99.66 (CH), 85.17 (CH), 69.76 (CH), 61.20 (CH$_2$), 39.94 (CH$_3$), 25.53 (CH$_3$), 18.14 (C), −5.42 (CH$_3$).

Preparation of 3-anilinycarbonyloxy-5-t-butyldimethylsilyloxy-2-desoxy-2,2'-difluorocytidine (NH$_4$)$_2$SO$_4$ (2 mg, 0.016 mmoles) was added to a solution of cytosine (0.31 g, 2.8 mmoles) in hexamethyldisilylamine (2.3 mL, 11.2 mmoles). The reaction mixture was stirred at 120° C. until it turned to a homogeneous solution (approximately 1.5 hours). The excessive hexamethyldisilylamine was removed under vacuum and a white powder was obtained.

To this powder was added anisole (3 ml), 3-anilinycarbonyloxy-5-t-butyldimethylsilyloxy-1-methanesulfonyloxy-2-desoxy-2,2'-difluororibose (65 mg, 0.14 mmoles), and NaI (0.1 g, 1.1 mmoles). The resulting mixture was then heated at 110° C. until TLC showed complete consumption of the ribose starting material (approximately 16 hours). The mixture was concentrated in vacuo to give a crude residue. This residue was dissolved in dichloromethane and washed with saturated aqueous NaHCO$_3$, dried over MgSO$_4$, and concentrated in vacuo to give 3-anilinycarbony-5-t-butyldimethylsilyloxy-2-desoxy-2,2'-difluorocytidine, in which the ratio of β and α anomor is 2:1.

$^1$H NMR (500 MHz, CDCl$_3$): δ 7.46 (d, 1 H, J=7.5 Hz), 7.0-7.4 (m, 5H), 6.38 (t, 1 H, J=7.5 Hz), 5.75 (d, 1 H, J=7.5 Hz), 4.42 (m, 1 H), 4.18 (m, 1 H), 3.72 (m, 2 H), 0.86-0.91 (m, 18 H), 0.06-0.10 (m, 12 H);

$^{13}$C NMR (125 MHz, CDCl$_3$): δ 165.45 (C), 155.44 (C), 141.70 (CH), 122.61 (C), 126 (C), 121.12 (C), 112 (CH), 106 (CH), 94.46 (CH), 85.40 (CH), 84.85 (q, CH, J$_{C-F}$=21 Hz), 71.73 (t, CH), 61.16 (CH$_2$), 25.65 (CH$_3$), 18.13 (C), −5.25 (CH$_3$).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, a 5-membered cyclic compound structurally analogous to the nucleoside compound mentioned above can also be made according to the process of the present invention. Thus, other embodiments are also within the claims.

What is claimed is:

1. A process comprising:
reacting a furan compound of the following formula:

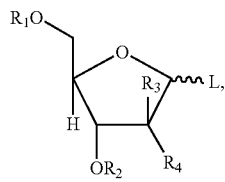

in which each of R$_1$ and R$_2$ independently is a hydroxy protecting group, or R$_1$ and R$_2$, together, are C$_{1-3}$ alkylene; each of R$_3$ and R$_4$ independently is H, halo, alkoxy, alkyl, or aryl, and L is a leaving group;

with a compound of the following formula:

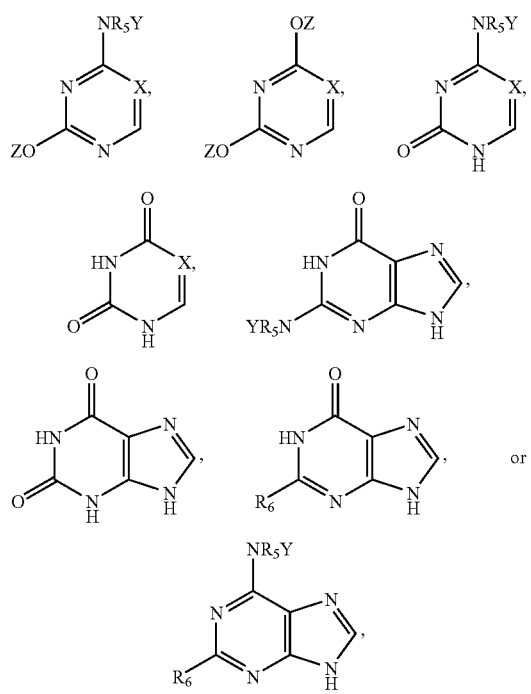

in which R$_5$ is H, alkyl, or aryl; R$_6$ is H, alkyl, alkenyl, halo, or aryl; X is N or C—R', R' being H, alkyl, alkenyl, halo, or aryl; Y is an amino protecting group; and Z is a hydroxy protecting group;

in the presence of a halide salt at 110-200° C. to stereoselectively form a β-nucleoside of the following formula:

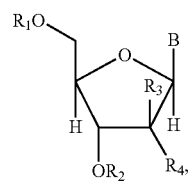

in which R$_1$, R$_2$, R$_3$, and R$_4$ are defined above and B is

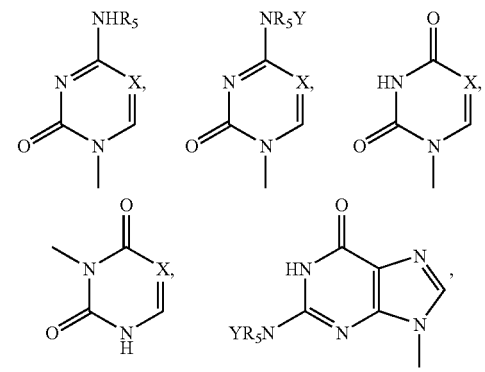

-continued

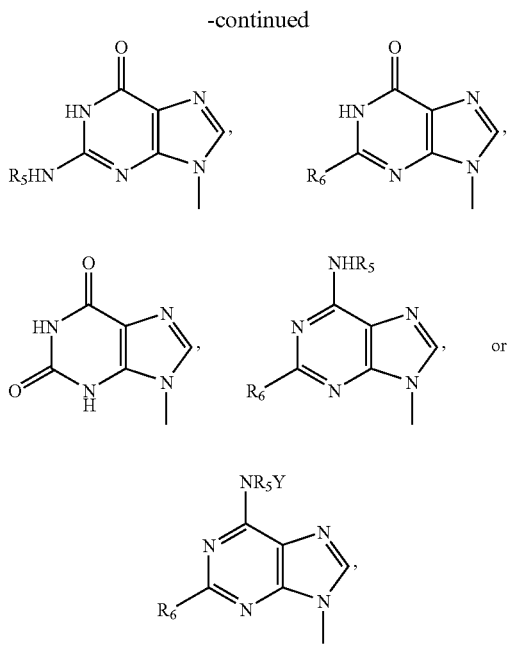

in which X, Y, $R_5$, and $R_6$ are defined above.

2. The process of claim 1, wherein $R_1$ and $R_2$ are different hydroxy protecting groups.

3. The process of claim 1, further comprising:
deprotecting the β-nucleoside to form a 3,5-dihydroxy β-nucleoside of the following formula:

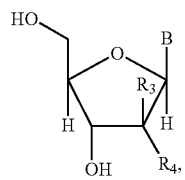

in which $R_3$, $R_4$, and B are as defined in claim 1.

4. The process of claim 3, wherein each of $R_3$ and $R_4$ is F.

5. The process of claim 3, wherein the halide salt is NaI or KI.

6. The process of claim 3, wherein the furan compound is reacted with

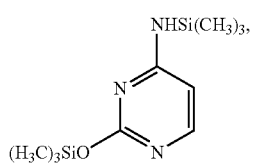

and the 3,5-dihydroxy β-nucleoside is

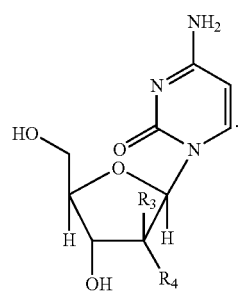

7. The process of claim 3, wherein L is methanesulfonate.

8. The process of claim 3, wherein $R_1$ and $R_2$ are different hydroxy protecting groups.

9. The process of claim 2, wherein $R_1$ is benzoyl, acyl, alkoxycarbonyl, or aminocarbonyl; and $R_2$ is silyl, benzyl, or benzyloxymethyl.

10. The process of claim 2, wherein $R_1$ is silyl, benzyl, or benzyloxymethyl; and $R_2$ is benzoyl, acyl, alkoxycarbonyl, aroxycarbonyl, or aminocarbonyl.

11. The process of claim 10, wherein $R_1$ is t-butyldimethylsilyl; and $R_2$ is aminocarbonyl.

12. The process of claim 11, wherein each of $R_3$ and $R_4$ is F.

13. The process of claim 12, wherein the halide salt is NaI.

14. The process of claim 13, wherein the furan compound is reacted with

and the 3,5-dihydroxy β-nucleoside is

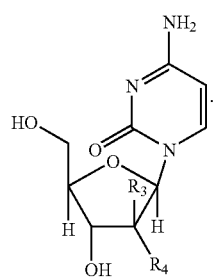

15. The process of claim 1, further comprising:
transforming a furanose of the following formula:

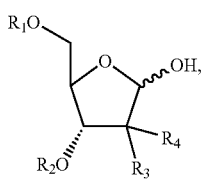

wherein $R_1$, $R_2$, $R_3$, and $R_4$ are defined in claim 1; to form the furan compound.

16. The process of claim 15, further comprising:
reducing a protected lactone of the following formula:

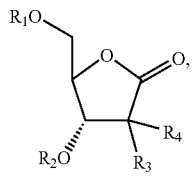

wherein $R_1$, $R_2$, $R_3$, and $R_4$ are defined in claim 1; to form the furanose.

17. The process of claim 16, further comprising:
converting an alcohol of the following formula:

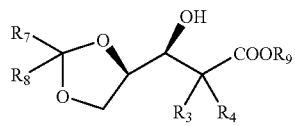

wherein $R_3$ and $R_4$ are defined in claim 1; each of $R_7$ and $R_8$ independently is H, halo, or alkyl; and $R_9$ is alkyl or aryl; to the protected lactone.

18. The process of claim 17, further comprising:
reacting an aldehyde of the following formula:

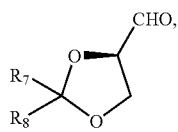

wherein $R_7$ and $R_8$ are defined in claim 17; with an ester of the following formula:

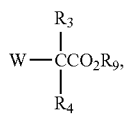

wherein $R_3$, $R_4$, and $R_9$ are defined in claim 17; to form the alcohol.

19. The process of claim 18, further comprising:
deprotecting the β-nucleoside to form a 3,5-dihydroxy β-nucleoside of the following formula:

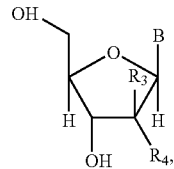

in which $R_3$, $R_4$, and B are as defined in claim 1.

20. The process of claim 19, wherein $R_1$ and $R_2$ are different hydroxy protecting groups.

* * * * *